United States Patent
Speeg et al.

(10) Patent No.: US 11,980,488 B2
(45) Date of Patent: May 14, 2024

(54) SURGICAL PROBE AND APPARATUS WITH IMPROVED GRAPHICAL DISPLAY

(71) Applicant: Devicor Medical Products, Inc., Cincinnati, OH (US)

(72) Inventors: Trevor W. V. Speeg, Williamsburg, OH (US); Michael E. Henley, Liberty Township, OH (US); Brian Michael Ruffner, Maineville, OH (US); Michael B. Watts, Potomac, MD (US); Harry Kyuhoon Ahn, Liberty Township, OH (US); Elijah Kreider, Hamilton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 18/111,672

(22) Filed: Feb. 20, 2023

(65) Prior Publication Data
US 2023/0200761 A1    Jun. 29, 2023

Related U.S. Application Data

(63) Continuation of application No. 17/513,980, filed on Oct. 29, 2021, now Pat. No. 11,612,365, which is a continuation of application No. 16/793,371, filed on Feb. 18, 2020, now Pat. No. 11,191,498, which is a continuation-in-part of application No. 16/659,802, filed on Oct. 22, 2019, now Pat. No. 10,905,387,
(Continued)

(51) Int. Cl.
| | | |
|---|---|---|
| A61B 6/00 | (2006.01) | |
| A61B 6/12 | (2006.01) | |
| A61B 6/40 | (2024.01) | |
| A61B 6/42 | (2024.01) | |
| G01T 1/161 | (2006.01) | |
| G01T 1/202 | (2006.01) | |
| G01T 1/24 | (2006.01) | |
| A61B 17/00 | (2006.01) | |

(52) U.S. Cl.
CPC .............. *A61B 6/4057* (2013.01); *A61B 6/12* (2013.01); *A61B 6/425* (2013.01); *A61B 6/4258* (2013.01); *A61B 6/4405* (2013.01); *A61B 6/4423* (2013.01); *G01T 1/161* (2013.01); *G01T 1/202* (2013.01); *G01T 1/244* (2013.01); *A61B 2017/00079* (2013.01); *G01T 1/2023* (2013.01)

(58) Field of Classification Search
CPC ......... A61B 6/12; A61B 6/425; A61B 6/4258; A61B 6/4405; A61B 6/4423; A61B 2017/00079; G01T 1/161; G01T 1/202; G01T 1/244; G01T 1/2023
See application file for complete search history.

(56) References Cited

FOREIGN PATENT DOCUMENTS

CN    201361118 Y  * 12/2009

* cited by examiner

*Primary Examiner* — Kiho Kim
(74) *Attorney, Agent, or Firm* — Frost Brown Todd LLP

(57) ABSTRACT

An apparatus for detecting a locating medium in tissue includes a probe, and a console. The probe includes a handle and a detector disposed on a distal end of the probe. The console is in communication and includes a display. The display has a first graphical representation and a second graphical representation. The first graphical representation is configured to depict a count real-time count based on a signal from the detector. The second graphical representation is configured to depict a target count.

20 Claims, 9 Drawing Sheets

Related U.S. Application Data which is a continuation of application No. 15/963,152, filed on Apr. 26, 2018, now Pat. No. 10,485,497, which is a continuation of application No. PCT/US2016/058907, filed on Oct. 26, 2016.

(60) Provisional application No. 62/806,949, filed on Feb. 18, 2019, provisional application No. 62/247,082, filed on Oct. 27, 2015.

SURGICAL PROBE AND APPARATUS WITH IMPROVED GRAPHICAL DISPLAY

PRIORITY

This application is a continuation of U.S. Ser. No. 17/513,980, entitled "Surgical Probe and Apparatus with Improved Graphical Display" filed Oct. 29, 2021, now published as U.S. Pub. No. 2022/0047231 on Feb. 17, 2022, which is a continuation of U.S. Ser. No. 16/793,371 entitled "Surgical Probe and Apparatus with Improved Graphical Display," filed Feb. 18, 2020, now published as U.S. Pub. No. 2020/200196964 on Jun. 25, 2020, which claims priority to U.S. Provisional Patent App. No. 62/806,949 entitled "Surgical Probe and Apparatus with Improved Graphical Display," filed on Feb. 18, 2019, the disclosure of which is incorporated by reference herein. U.S. Ser. No. 16/793,371 is further a continuation-in-part of U.S. Ser. No. 16/659,802 entitled "Surgical Probe and Apparatus and System and Method of Use Thereof," filed on Oct. 22, 2019, which is a continuation of U.S. Ser. No. 15/963,152 entitled "Surgical Probe and Apparatus and System and Method of Use Thereof," filed Apr. 26, 2018, now issued as U.S. Pat. No. 10,485,497 on Nov. 26, 2019, which is a continuation of International App. No. PCT/US2016/058907 entitled "Surgical Probe and Apparatus and System and Method of Use Thereof," filed on Oct. 26, 2016, which claims priority to U.S. Provisional Patent App. No. 62/247,082, entitled "Surgical Probe and Apparatus and System and Method of Use Thereof," filed on Oct. 27, 2015, the disclosures of which are incorporated by reference herein.

BACKGROUND

Procedures for the treatment of cancer generally have been based upon the natural history of tumor spread, and thence, upon operative and non-operative options available to the physician. Operative options generally have looked to the physical identification and surgical resection of tumor. A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) Typically, large tumor is readily located by the surgeon by visualization at the operating theater, and, in particular, through palpation, i.e., the feel of tumor as opposed to that of normal tissue. To achieve operative success, however, it is necessary for the surgeon to somehow locate "occult" tumor, i.e., tumor which cannot be found by the conventional surgical procedures of sight and feel. Failure to locate and remove such occult tumor generally will result in the continued growth of cancer in the patient, a condition often referred to as "recurrent" cancer.

A method for locating, differentiating, and removing neoplasms uses a radiolabeled antibody injected into the patient. Once injected, such antibodies are known to accumulate in neoplastic tissues at a higher concentration than in normal tissue. A portable radiation detection probe is employed by a surgeon intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure is now known as radioimmunoguided surgery, or RIGS® (RIGS being a registered trademark of Neoprobe Corporation of Dublin, Ohio).

Similarly, Intraoperative Lymphatic Mapping (ILM) may be utilized to study the effect of neoplastic tissue on a patient's lymphatic system. The lymphatic system provides a vital function in fighting disease; however, this intricate network also creates an ideal pathway for cancer cells to travel and spread. For example, certain solid-tumor cancers such as breast, melanoma, lung, colorectal and head-and-neck cancer frequently spread via the lymphatic system.

The spread of cancer to the patient's lymph nodes is typically determined by examination of the nodes along the likely drainage path by pathology to determine if tumor cells are present. It is not uncommon for a surgeon to remove most of the lymph nodes in the area surrounding a solid tumor. This radical and often unnecessary procedure causes a large number of patients to experience significant complications following surgery.

ILM overcomes many of these drawbacks. In an ILM procedure, a tracing agent such as a radioactive, magnetic, fluorescent, microwave, radio frequency emitting, or other material is injected at the site of the primary tumor. Following injection, the tracing agent follows the likely drainage path of the tumor to the initial lymph node or nodes that the tumor may be draining to, referred to as the "sentinel node(s)." A detection device such as a gamma radiation, magnetic field, radio frequency, or other detection device is used to detect the tracing agent. Since the lymph nodes are connected, oncologists believe that if the sentinel nodes show no sign of malignancy, then the downstream nodes in the pathway are likely to be clear of disease, as well. As such, the removal of other nearby lymph nodes would be deemed clinically unnecessary. Therefore, the ability to rapidly locate and biopsy sentinel nodes provides vital information to the physician in determining if the cancer has spread or if it is localized to the site of the primary tumor.

Surgical radiation detection instrumentation is comprised generally of a hand-held probe which is in electrical communication with a control console via a flexible cable. This control console is typically located within the operating room facility but out of the sterile field, while the hand-held probe and forward portions of its associated cable are located within that field. The hand-held radiation detecting probe is relatively small and performs in conjunction with a detector such as a cadmium zinc telluride (CZT) crystal. Details of such instrumentation may be found in commonly owned U.S. Pat. No. 4,782,840, the disclosure of which is expressly incorporated herein by reference.

A drawback of current surgical radiation detection instrumentation is the flexible cable extending between the probe and the control console. If the cable is too short, it tends to limit the user's flexibility in positioning the probe. Conversely, if the cable is too long it may become entangled with other instrumentation and equipment. Furthermore, a cable that is not adequately or appropriately sterilized or draped is a potential source of contamination of the operative field.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
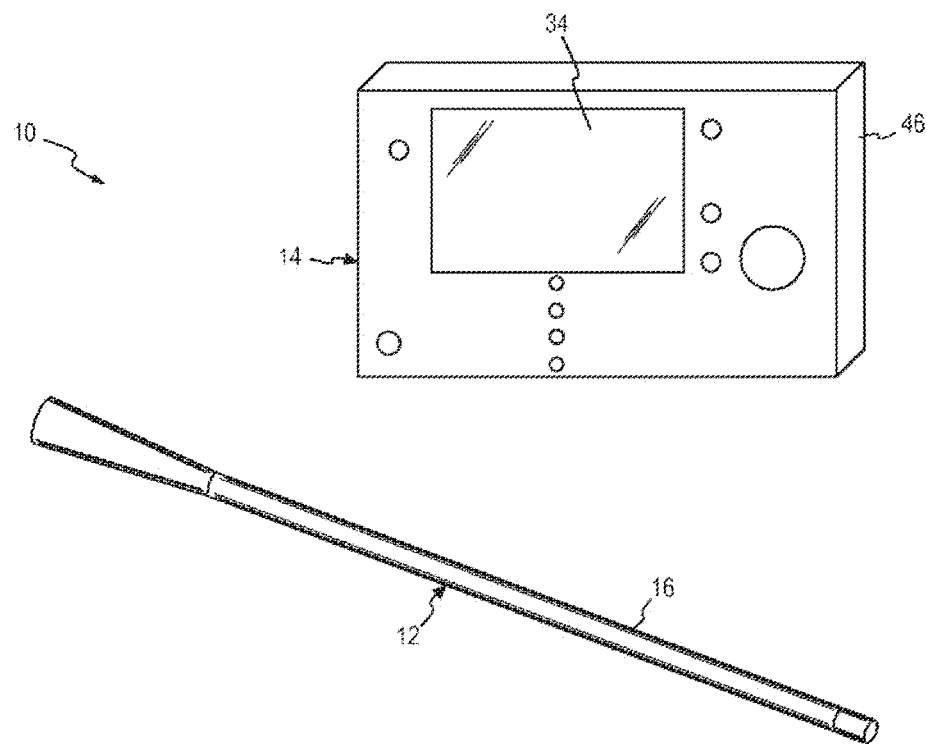
FIG. 1 shows a system for detecting and locating sources of radiation emission comprising a probe and an associated instrumentation console according to an embodiment of the present invention.

The general arrangement of a system (10) for detecting and locating sources of radiation emission is shown in FIG. 1 according to an embodiment of the present invention. System (10) comprises a probe (12) that is in wireless communication with an associated instrumentation console (14). Further details of each are provided below.

A. Probe

Figure 2:
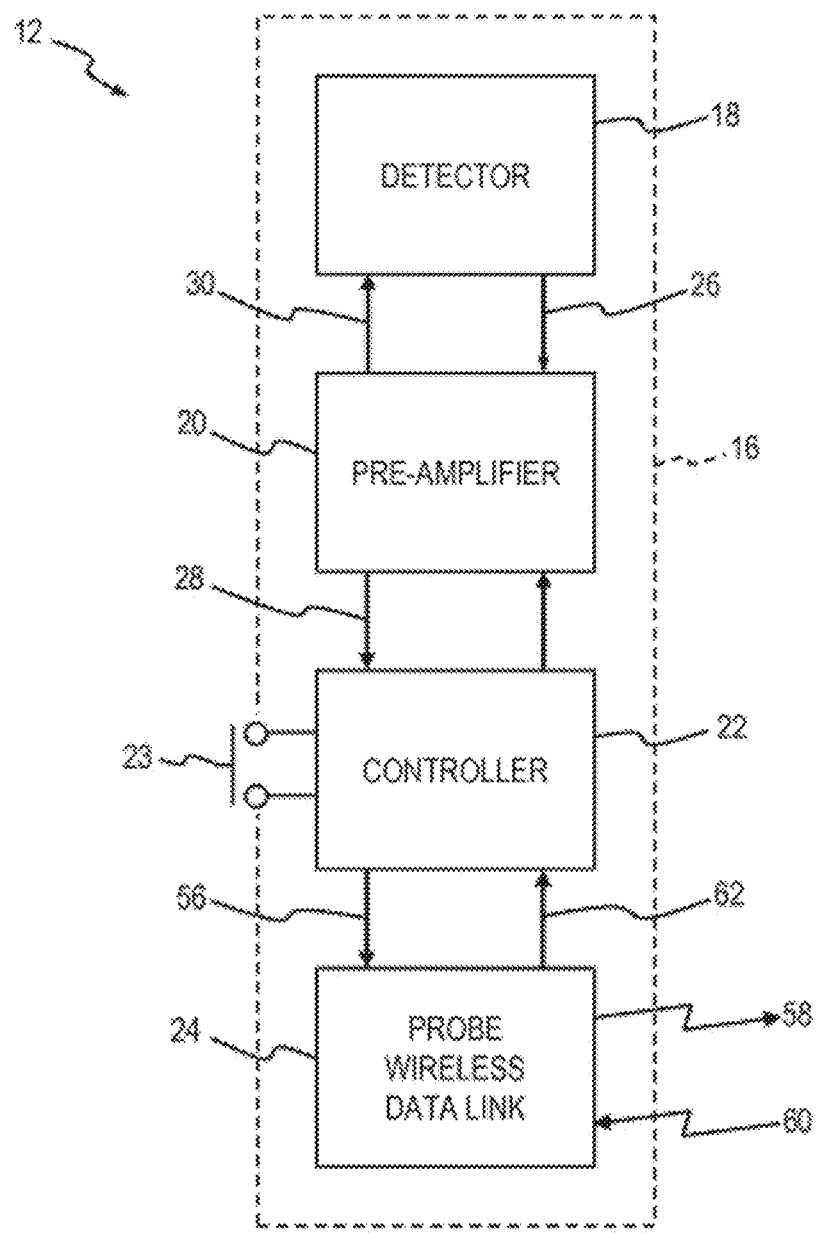
FIG. 2 is a block diagram of the probe of FIG. 1.

With reference to FIGS. 1 and 2, probe (12) includes a housing (16) containing in pertinent part a detector (18), a preamplifier (20), a controller (22) and a probe wireless data link (24). Probe (12) is powered by a not-shown power source, such as a disposable or rechargeable battery.

Detector (18) generates a low-level electrical signal (26) corresponding to the gamma radiation count of tissue proximate the detector. Detector (18) may be made from cadmium zinc telluride or any other semiconductor material suitable for detecting photon radiation. More broadly, detector (18) may be made from any suitable type of crystal that is responsive to gamma radiation emitted by radiolabeled antibodies. For example, detector (18) may comprise cadmium-telluride crystals with or without an alloy, for example, with zinc. Such alloys for the present description may generally and interchangeably be referred to as "Cadmium-telluride," "CdTe" and "CZT." Details of exemplary CZT crystals may be found in commonly assigned U.S. Pat. Nos. 6,218,669, 6,191,422, 5,495,111 and 5,441,050, the entire contents thereof being incorporated herein by reference thereto.

Alternatively, detector (18) may be a scintillating device. The scintillating device may be any type of particle or radiation detector now known or later developed for detecting and counting scintillations produced by ionizing radiation including, but not limited to, cesium iodide. For example, detector (18) configured as a scintillating device may operate through emission of light flashes that are detected by a photosensitive device, such as a photomultiplier or a silicon PIN diode.

Preamplifier (20) receives and amplifies the low-level electrical signal (26) generated by detector (18) to a corresponding output electrical signal (28) of greater magnitude (i.e., voltage and current). Preamplifier (18) may also supply an electrical bias voltage (30) to detector (18) to effect charge migration in the detector when it is exposed to gamma radiation. Details of exemplary preamplifiers may be found in commonly assigned U.S. Pat. Nos. 6,222,193 and 6,204,505, the entire contents thereof being incorporated herein by reference.

Controller (22) receives the output electrical signal (28) from preamplifier (20) and analyzes the output electrical signal to derive gamma data corresponding to the amount of gamma energy detected by detector (18). In some embodiments the gamma data may be in the form of "counts" relating to the number of detected photon radiation impingements. Further details may be found in commonly assigned U.S. Pat. No. 4,889,991, the entire contents thereof being incorporated herein by reference thereto. Controller (22) may also be configured with a control switch (23) to allow a user of probe (12) to set predetermined operating parameters of the probe including, without limitation, a real-time radiation target count and a time-interval accumulated count, and calibration/test. Parameters may be selected by actuating control switch (23) for a predetermined period of time, or by actuating the control switch a predetermined number of times within a predetermined period of time.

Controller (22) may be a digital microprocessor-based control unit configured to operate according to a predetermined control logic to provide control signals for controlling the operation of probe (12). Alternatively, controller (22) may comprise other types of digital-based architectures utilizing, for example, a computer, microcontroller, programmable logic device and the like. The control logic of controller (22) may be defined by a set of predetermined instructions, such as a computer program or "fuzzy logic." Controller (22) may also comprise analog circuitry in whole or in part.

Probe wireless data link (24) (hereinafter termed "probe link (24)") is configured for operation in conjunction with an associated instrumentation console data link (32) of console (14) to transfer data between the probe and the console. Probe link (24) may be implemented in any form now known or later invented utilizing, without limitation, radio frequency (RF), visible light, infra-red light, sonic and ultrasonic links and any conventional type of analog or digital modulation including, without limitation, amplitude modulation, frequency modulation, phase shift keying and frequency shift keying. Telecommunication protocols such as the BLUETOOTH® standard as promulgated by the Bluetooth Special Interest Group, Inc. (SIG) may also be employed. An example embodiment employing a BLUETOOTH protocol is further described below. Alternatively, a proprietary communication protocol may be utilized.

B. Instrumentation Console

Figure 3:
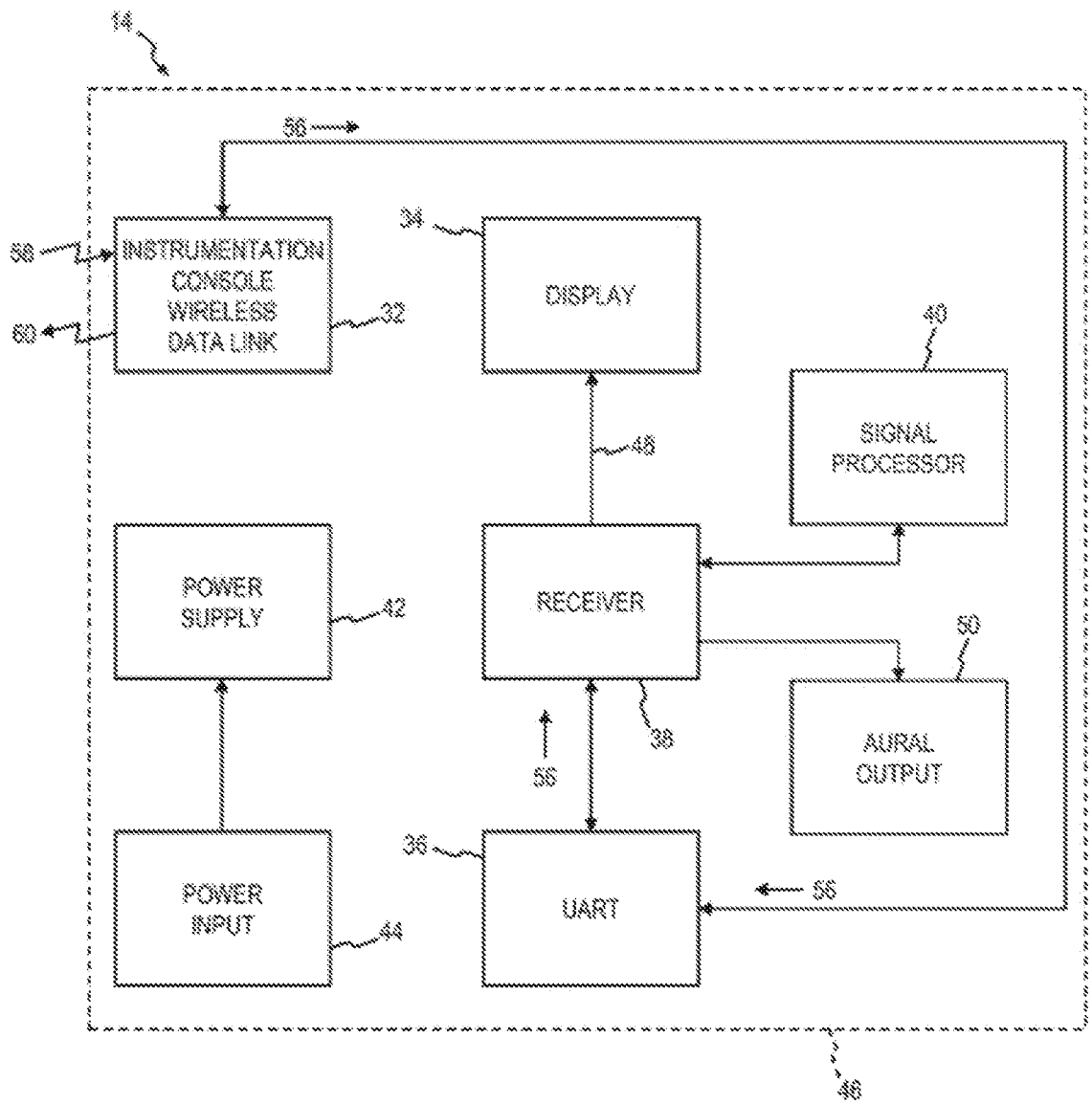
FIG. 3 is a block diagram of the instrumentation console of FIG. 1.
Figure 4:
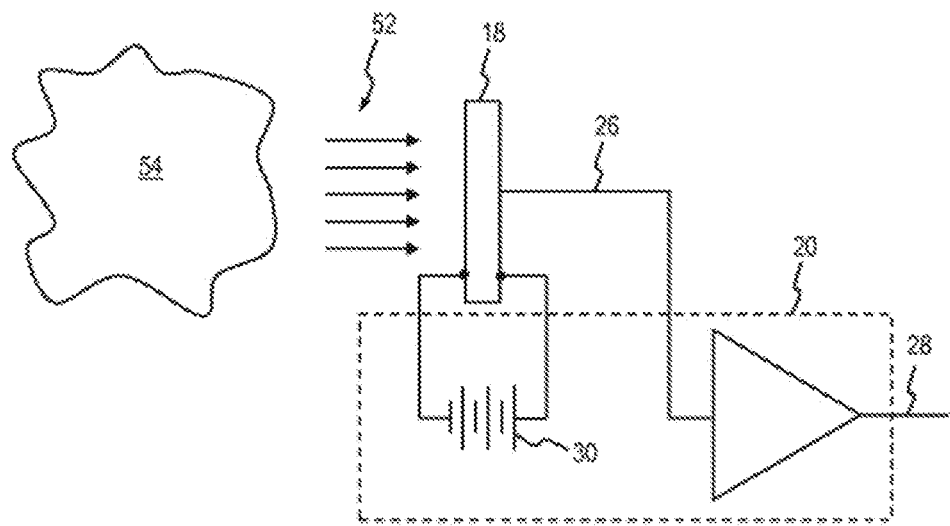
FIG. 4 is a partial schematic diagram of the probe of FIG. 1.

With reference to FIGS. 1 and 3, instrumentation console (14) includes an integral instrumentation console wireless data, link (32), a display (34), a universal asynchronous receiver/transmitter (UART) (36), a receiver (38), a signal processor (40), a power supply (42) and a power input (44).

Integral instrumentation console wireless data link (32) (hereinafter termed "console link (32)") is integral to, and contained by, a housing (46) of console (14). Console link (32) is configured for operation in conjunction with probe link (24) to transfer data between the probe (12) and instrumentation console (14). Console link (32) may be implemented in any form now known or later invented utilizing, without limitation, radio frequency (RF), visible light, infra-red light, sonic and ultrasonic links and any conventional type of analog or digital modulation including, without limitation, amplitude modulation, frequency modulation, phase shift keying and frequency shift keying. Telecommunication protocols such as the BLUETOOTH® standard as promulgated by the Bluetooth Special Interest Group, Inc. (SIG) may also be employed. A standard Serial Port Protocol (SPP) software package may also be included with console link (32). Alternatively, a proprietary communication protocol may be utilized.

UART (36) is a data communication interface and converter. UART (36) converts data received by console link (32) to a serial data stream and forwards the serial data stream to receiver (38). Likewise, serial data generated by receiver (38) may be forwarded to console link (32) via UART (36) and converted to another data format for transmission to probe (12) via links (24), (32). The serial data stream employed in conjunction with UART (36) may be configured in an Electronic Industries Alliance (EIA) serial data format, such as RS-232, RS-422 and RS-485, or may be a proprietary format.

Receiver (38) receives the serial data stream from UART (36) and converts the serial data stream to electrical display signals (48) having predetermined voltage, current and frequency values corresponding to the content of the data stream. Electrical display signals (48) are coupled to display (34).

Receiver (38) may include a digital microprocessor-based control portion configured to operate according to a predetermined control logic to provide control signals for controlling the operation of instrumentation console (14). Alternatively, receiver (38) may comprise other types of digital-based architectures utilizing, for example, a computer, microcontroller, programmable logic device and the like. The control logic of receiver (38) may be defined by a set of predetermined instructions, such as a computer program or "fuzzy logic." In still other embodiments receiver (38) may be partially or wholly comprised of analog circuitry. Receiver (38) may incorporate, without limitation, any or all of the gamma detection features discussed in commonly assigned U.S. Pat. Nos. 6,272,373, 6,259,095, 6,144,876 and 5,732,704, the entire contents thereof being incorporated herein by reference thereto.

Signal processor (40) may be configured to execute functions relating to analyzing, interpreting and manipulating the serial gamma data. Functions executed by signal processor (40) include, without limitation, filtering, smoothing, noise reduction and thresholding. For example, signal processor (40) may be adjusted by a user of system (10) to set a threshold value of the gamma data such that data having a value below the select threshold is ignored by receiver (38) and not provided to display (34) in the form of electrical display signals (48). A dynamic pitch mode may be selected wherein a baseline value is stored and used as a threshold. Alternatively, a binary pitch mode may be selected wherein a baseline value is stored for comparison, to determine whether a difference in detected radioactivity between a reference (such as background tissue) and a radiation source (such as target tissue) is statistically significant. Signal processor (40) may be configured for use with analog or digital signals, or both.

Display (34) receives electrical display signals (48) and converts the display signals to a visually perceivable indication corresponding to the serial data stream. Display (34) may be any type of visual display now known or later developed including, without limitation, cathode ray tubes, fixed-format liquid crystal displays, plasma displays, active matrix liquid crystal displays, and light emitting diode displays. Display (34) may be monochromatic, color or a combination thereof, and may include a backlight.

Instrumentation console (14) may optionally include, an aural output subsystem (50) configured to generate an aural signal corresponding to the gamma data in a predetermined manner. For example, the frequency and/or amplitude of the aural signal may be made proportional to a gamma count corresponding to the low-level electrical signal (26) generated by detector (18).

Power supply (42) may be any type of linear or switching-type arrangement for converting mains AC power to one or more predetermined AC and DC voltages and currents required by the components of instrumentation console (14).

Power input (42) may be configured to establish a select AC mains power input, such as 110 or 220 volts AC. Power input module (42) may also include over-voltage protection circuitry, such as transient suppressors, and over-current protection devices, such as fuses and circuit breakers.

C. System Operation

With reference now to FIGS. 1 through 4 together, in operation system (10) detector (18) of probe (12) is electrically biased by bias voltage (30) coupled thereto. Gamma radiation (52) emitted from a source (54) of photon emission radiation impinges upon detector (18), causing the detector to generate a low level electrical signal (26) corresponding to predetermined characteristics of the detected gamma radiation, such as the number of photon impingements or radiation count (hereinafter generally termed "gamma data"). Preamplifier (20) receives and amplifies low-level electrical signal (26) generated by detector (18) to a corresponding output electrical signal (28) of greater amplitude, the output electrical signal likewise corresponding to and representing the gamma data.

Controller (20) receives the gamma data from preamplifier (20) via output electrical signal (28). Controller (20) converts the gamma data to a "message" (56) having a predetermined analog and/or digital format, the message containing information relating the gamma data in said format, Message (56) is periodically transmitted as a component of a probe output signal (58) transmitted by probe link (22) to console link (24). In one embodiment of the present invention message (56) is transmitted about every fifty milliseconds. Message (56) contains a start transmission character, a message type character, the gamma data (two bytes), and a checksum byte (summing all other message bytes). Probe output signal (58) may also include error correction and automatic re-transmission capability to ensure the quality of the data transmission. If BLUETOOTH technology is employed, links (22), (24) may include a frequency hopping technique to avoid interference with other wireless devices.

A self-correction scheme is preferred for probe output signal (58). If probe output signal (58) lacks such self-correction, a stronger message check such as a 16-bit cyclic redundancy check, or CRC may be used. Furthermore, if probe output signal (58) lacks automatic re-transmission, a bidirectional transmitter-receiver handshake scheme may be utilized wherein a console output signal (60) issued wirelessly by console link (32) transmits a confirmation message (62) to probe link (24), the confirmation message being forwarded to controller (22) by the probe link for error-checking comparison with message (56).

Console link (24) forwards message (56) to UART (36), which converts the message to serial format and forwards the message to receiver (38). Receiver (38) validates message (56) using a checksum byte. Once the message is validated, the received gamma data is compared against the last counter value and a difference is calculated. Any 16-bit counter overflow is also taken into account. If the gamma data is in the form of an absolute gamma count a difference calculation is desirable.

The gamma count value is synchronized to a highly accurate internal five millisecond time interval by receiver (38), each time interval being termed a "bin." This synchronization is accomplished so that a stable, accurate gamma data count provided to display (34) in the form of electrical display signals (48), the electrical display signals being converted by the display to a corresponding visually perceivable image representative of the gamma data. Incoming gamma data values are averaged by receiver (38) over the next ten "bins" to derive a smoothed gamma data count. The smoothing operation is preferably configured so that it does not add or remove any gamma counts to the resulting values.

If messages (56) are being lost (i.e., wireless out of range, transmitter turned off, or wireless interference), the gamma data values displayed by display (34) may be set to zero. If no messages are detected for a predetermined minimum period of time, such as for five seconds, receiver (38) may determine that probe output signal (58) has been lost and provides predetermined electrical display signals (48) to display (34) such that the display visually indicates this condition to a user of system (10) in a predetermined manner, such as with a "NO SIGNAL" annunciation.

In some embodiments of the present invention receiver (38 may be coupled to signal processor (40). Signal processor may be configured to execute some or all of the previously noted functions relating to analyzing, interpreting and manipulating the serial gamma data.

In some embodiments of the present invention aural output subsystem (50) may be used in conjunction with display (34), or instead of the display. Aural output subsystem (50) may be configured to generate an aural signal corresponding to the gamma data in a predetermined manner. For example, the frequency and/or amplitude of the aural signal may be proportional to the gamma count.

In previous gamma detection diagnostic systems analog signals from a probe were coupled to a console through a flexible cable. The assignee of this application has previously improved upon the art by developing a wireless link between a probe and a console, but that configuration required an external adapter coupled to a data interface connector of the console. The external adapter is subject to being lost or misplaced, or could be accidentally unplugged, thereby disrupting diagnostic activities that often have been planned well in advance of the procedure. Furthermore, repetitive insertion and removal of the external adapter to the data interface of the console can generate wear of mating connectors on the adapter and console, resulting in intermittent or broken connections. The present invention, which includes a probe (12) having a probe link (22) that communicates with a corresponding console link (24) that is integral to a console (14), represents a significant improvement in the art.

D. Multi-Display Instrumentation Console

Figure 5:
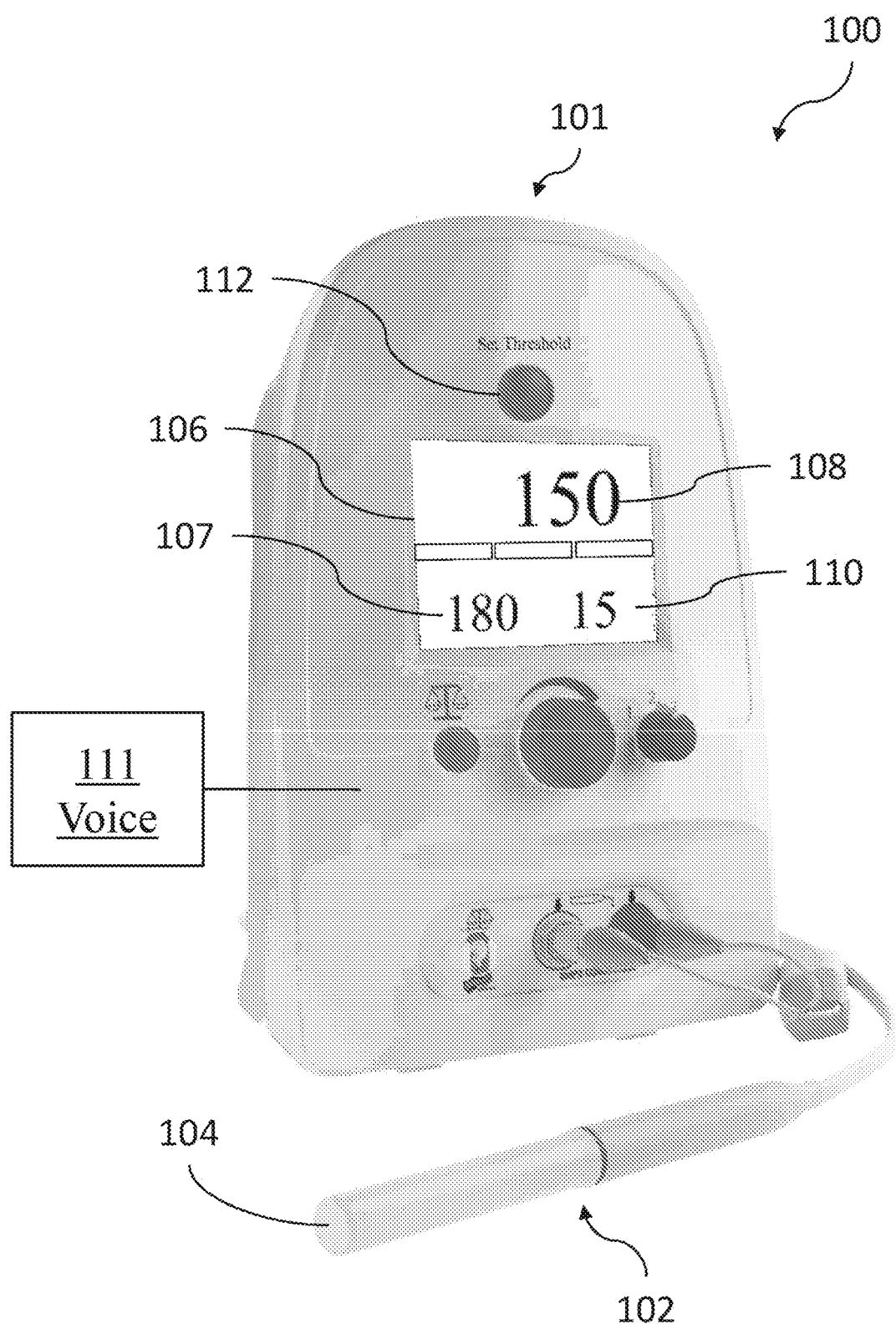
FIG. 5 shows a system for detecting and measuring a material within a human body.

FIG. 5 shows a system (100) for detecting radiation, magnetic fields, and other signals. A probe (102) may be used similarly to the probe (12), and may be moved about a patient in order to detect and measure the strength of a substance or material injected in the patient during a procedure such as those described herein. A probe tip (104) may contain a sensor configured to detect magnetic field strength, gamma ray or other radiation, incoherent and coherent light, microwave, radio frequency, fluorescence, and other conditions or signals associated with or emitted by an injected material, substance, or other tracing agent. As one example, a tracing agent might be a magnetic material reduced into a powder or grit and mixed with a carrier liquid or fluid.

An instrumentation console (101) includes a display (106) configured to display one or more characteristics measured by the probe (102). The instrumentation console (101) may have one or more characteristics or features as described above in the context of the instrumentation console (14). The display (106) may show any of the information or features described herein, and may also show a current measurement (108), a max measurement (107), and a threshold (or target) measurement (110). The current measurement (108) may be the strength of a signal or field currently detected by the probe (102).

The max measurement (107) may be the maximum measured strength of a signal or field during a particular use of the probe (102) (e.g., during a procedure the highest measured strength may be 180, and may be automatically stored until replaced by a higher measured strength). The threshold measurement (110) may be automatically determined based upon the current measurement (108) or the max measurement (107), and may be determined as a static or other proportion of the measured value. For example, the threshold measurement (110) may be determined as 10% of the current measurement (108), and may be saved and displayed when a threshold button (112) is pressed by a user during a procedure. Percentages might be statically configured for each device, or may be variably configured by a user for each device or procedure performed with a device, or may be automatically configured based upon a selection of a type of procedure, or may be set or configured in other similar ways. This may be useful to set a detection threshold during a procedure so that a user of the probe (102) may easily determine when they have reached a portion of the patient's body that is unlikely to have received substantial portions of the injected material. The instrumentation console (101) may also include a voice detection feature (111) such as a microphone and software for interpreting voice commands from a user, and that may be used similarly to the threshold button (112) or any other control. The voice detection feature (111) and threshold button (112) may be used in addition to or as an alternative to other control features described herein, and may be combined with other control features such as foot pedals, motion controls, inductive controls, and other control types that may be combined with one or more of the system (100), instrumentation console (101), or probe (102).

In some examples, threshold measurement (110) can be shown as a simple numerical representation of a number of counts over a predetermined period of time (e.g., counts per second). In other examples, threshold measurement (110) can be shown as a graphical representation depicting the relationship between threshold measurement (110) and current measurement (108) and/or max measurement (107). By way of example only, such a graphical representation may be in the form of a color coded bar graph that changes in color intensity as current measurement (108) approaches threshold measurement (110). In still other examples, threshold measurement (110) can be shown as both a numerical representation and a graphical representation concurrently. In addition, it should be understood that in some examples one or more components of display (106) can be optionally incorporated into a portion of probe (102). For instance, in some examples threshold measurement (110), current measurement (108), max measurement (107) and/or a graphical representation of one or more such measurements can be integrated within a portion of probe (102) such as on a handle.

Figure 6A:
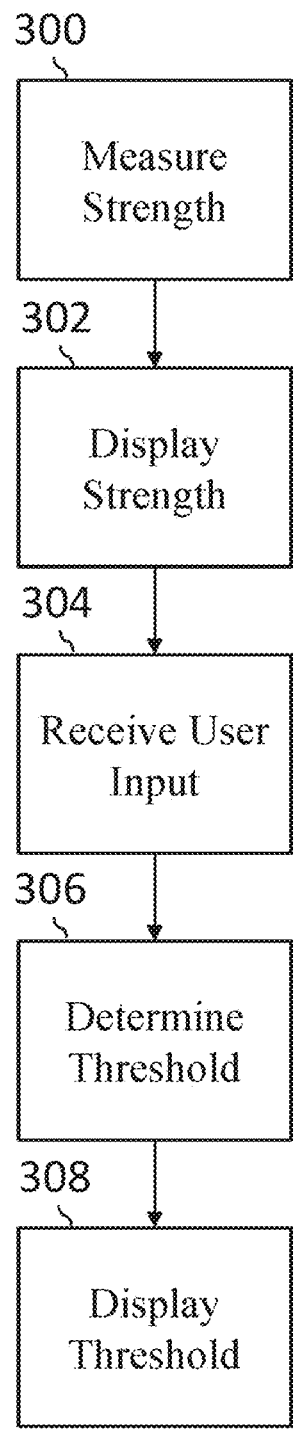
FIGS. 6A and 6B are flowcharts of exemplary steps that may be performed with the system of FIG. 5 to display measured signals.

FIG. 6A shows an example of the operation of the system (100), the system may measure (300) the strength of a signal and display (302) that strength as the current measurement (108). When a user input is received (304), such as an actuation of the threshold button (112), a threshold may be determined (306) as a percentage of the current measurement (108), and then displayed (308).

Figure 6B:
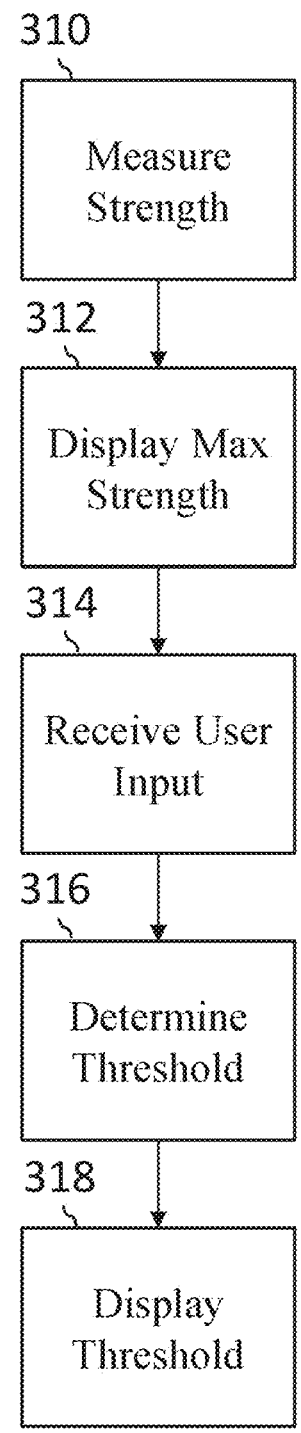

FIG. 6B shows another example of the operation of the system (100), the system may measure (310) the strength of a signal and, when that strength is a maximum for that session or use, display (312) that max strength as the max measurement (107). When a user input is received (314), such as an actuation of the threshold button (112), a threshold may be determined (316) as a percentage of the max measurement (107), and then displayed (318).

E. Magnetic Probe System

Figure 7:
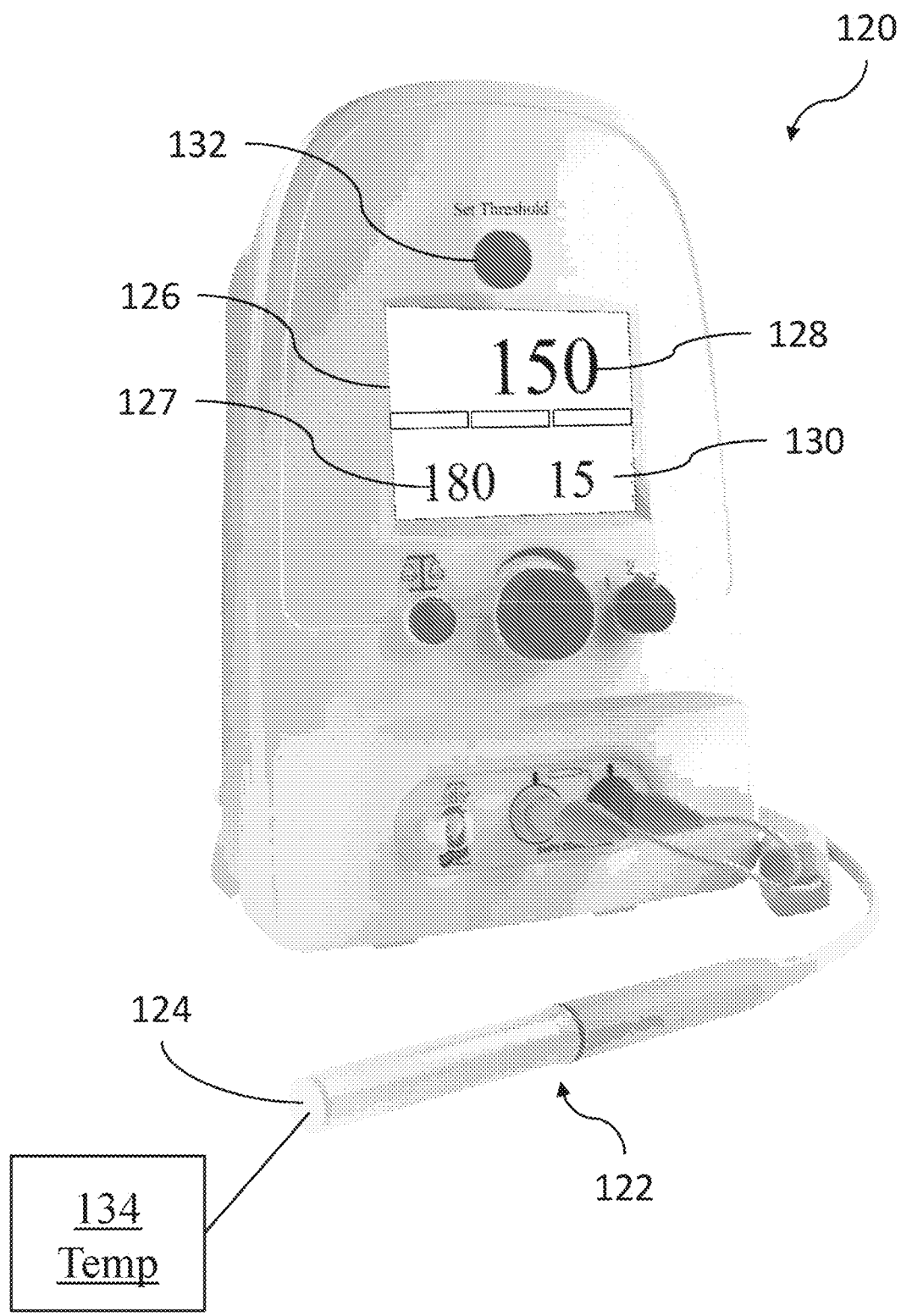
FIG. 7 shows a system for detecting and measuring magnetic fields within a human body.

FIG. 7 shows a system (120) having one or more of the features or functions of the system (10) and system (100). The system (120) includes a probe (122) and probe tip (124) usable to detect and measure the strength of an injected material or substance. The probe (122) may also include a temperature sensor (134) proximate to the probe tip (124) and configured to detect the temperature of the surrounding area (e.g., a procedure room, patient tissue). The system (120) may also include a display (126) configured to display a current measurement (128), max measurement (127), and threshold measurement (130), as well as a set threshold button (132), as described in the context of the system (100).

Figure 8:
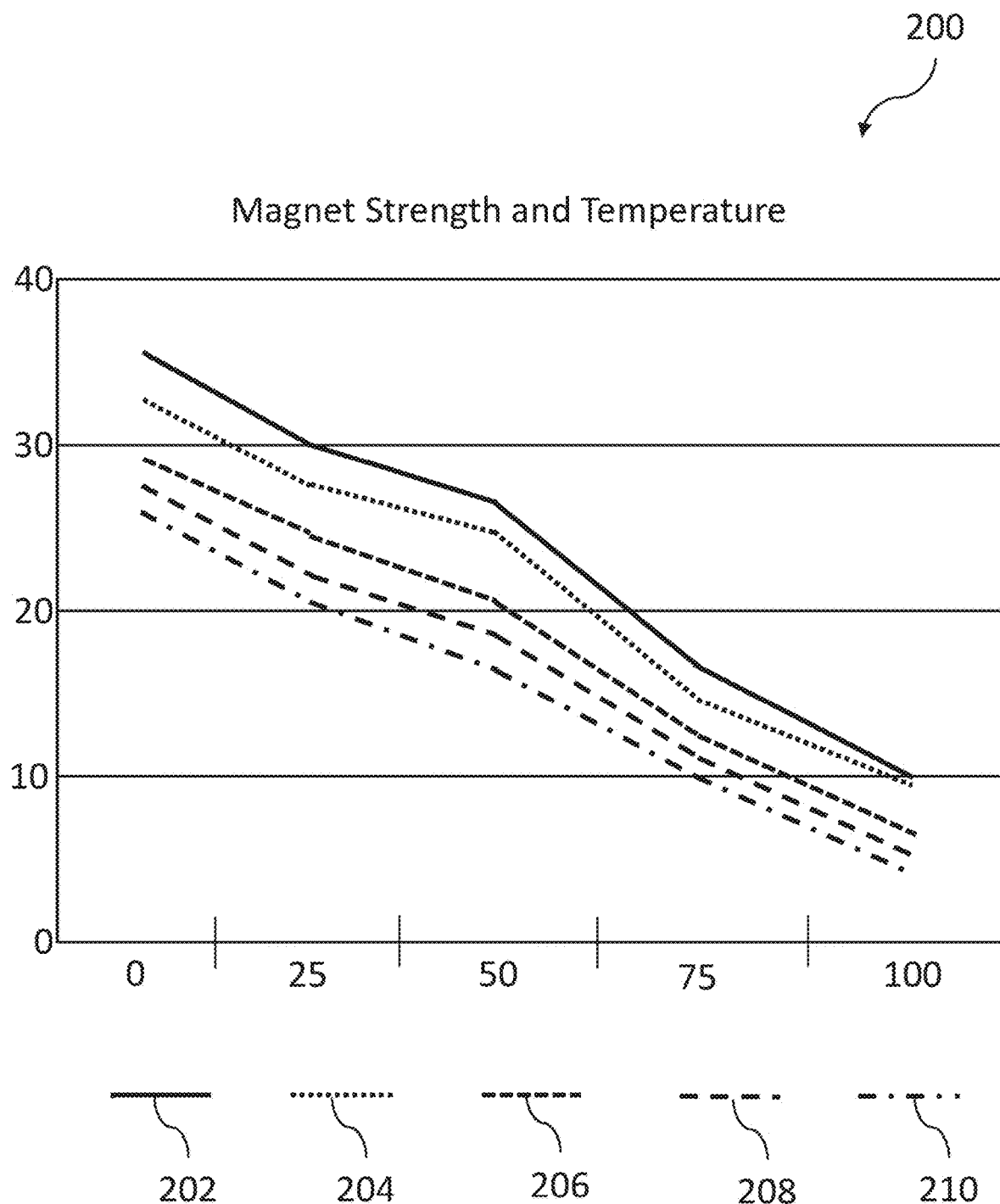
FIG. 8 is a graph illustrating a relationship between magnetic strength and temperature.

The probe tip (124) may be implemented as a sensor configured to detect magnetic field strength, which may be used to detect the movement of magnetic particles that have been injected into a patient. Magnetic field detection in this manner may be influenced by the temperature of the magnets. For example, FIG. 8 shows a graph (200) illustrating a relationship between magnetic strength and temperature. A y-axis of the graph (200) shows a number of magnetic washers or elements picked up by a certain magnet, while the x-axis shows a temperature of the magnet in Celsius. The graph lines (202, 204, 206, 208, 210) each show the results for a different type of magnet at various temperatures.

Figure 9:
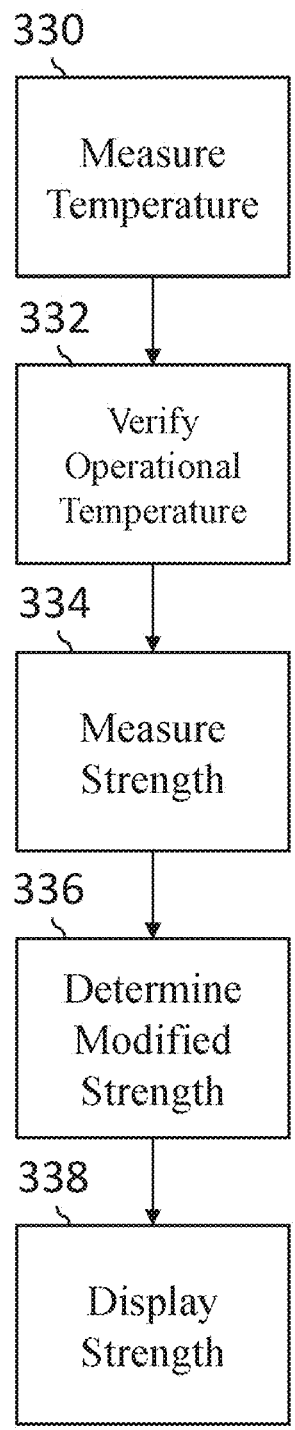
FIG. 9 is a flowchart of exemplary steps that may be performed to operate the system of FIG. 7 based on temperature.

To account for variations in magnetic field detection as a result of temperature, the temperature sensor (134) may be used to detect the temperature of the patient and calibrate the magnetic field detection based thereon. FIG. 9 shows an example of the system (100) calibrating magnetic detection in this manner. The temperature may be measured (300) using the temperature sensor (134). In some implementations, the system (120) may verify (332) that the probe (122) is at an operational temperature. Where the probe (122) is too cold (e.g., such as where it has been stored in a cold area) or too hot, the system (120) may prevent used of the probe until it reaches acceptable operational temperatures. Once operational, a strength of the magnetic field may be measured (334), and the measured temperature and measured field strength may be used to determine (336) a modified or calibrated measured strength, which may then be displayed (338).

While this invention has been shown and described with respect to a detailed embodiment thereof, it will be understood by those skilled in the art that changes in form and detail thereof may be made without departing from the scope of the claims of the invention. Any one or more of the following examples may be fully or partially combined with each other as described herein.

EXAMPLE 1

A surgical apparatus for locating lymph nodes for selective removal which includes a display, processor, GUI, memory, proximity sensor and probe. The proximity sensor located in the probe senses the strength of the signal from the source and continuously displays a strength indicator in realtime. The strength indicator could include a numerical value and bar indicator. It could also include sound. The apparatus includes a button on the front panel (either inside the display screen or outside of it in the housing) or foot pedal that when pressed will display a 10% (preselected secondary node threshold) of the current strength indicator value and display it on a separate part of the screen on a permanent basis until the same button or foot pedal is pressed again.

EXAMPLE 2

A surgical apparatus that displays two values (max count value and threshold value (10% of the max count value)) on the display in addition to the realtime updating strength indicator, with the two values configured to be automatically updated as the probe is being used.

EXAMPLE 3

A surgical apparatus configured to set a max value based upon an input from a foot pedal or a voice activation, to cause the console to save and display that value under the max count value as well as the threshold value, wherein the threshold value may be 10% of the set value, and further configured to clear one or more values based on a further voice command or foot pedal input.

EXAMPLE 4

A surgical apparatus that allows a user to program secondary node threshold percentage, and configured to default to 10%, but be programmable to a new value by the user based upon a user desired value or new research on threshold percentage.

EXAMPLE 5

A surgical apparatus that uses the foot pedal to toggle between automatic updating of max count value/threshold value, and holding of those values.

EXAMPLE 6

The surgical apparatus of example 5, wherein a first tap of the foot pedal holds a value and a second tap of the foot pedal releases a value.

EXAMPLE 7

The surgical apparatus of example 5, wherein a voice command causes the apparatus to hold a value, and a second voice command causes the apparatus to release a value.

EXAMPLE 8

A surgical apparatus that includes a temperature sensor in a probe or instrumentation console configured to automatically compensate for the temperature drift of the signal when detecting proximity or signal strength of a material wherein the material or probe are affected by temperature such that the measured strength at a fixed distance has an inverse relationship, such that the higher the temperature the lower the measured strength, wherein the relationship is used to assist in calibrating and adjusting the field strength value for detection during use, and continuously adjust for the temperature related drift as the probe temperature could be affected by the temperature of the person being examined depending how close the probe tip is to tissue.

EXAMPLE 9

A surgical apparatus wherein if the temperature sensor detects an abnormally low or high temperature outside of the operating temperature range, the processor in the control module is configured to prevent the operation of the apparatus, wherein the processor is configured determine when the temperature is within a usable range and allow operation of the apparatus, and wherein the processor is configured to use the temperature drift graph to adjust the realtime count value based on the sensed temperature value.

EXAMPLE 10

A surgical apparatus comprising an instrumentation console and a probe, wherein the probe is configured to measure a concentration of a tracing agent injected into a patient by placing the probe proximate to a portion of the patients body, and wherein the instrumentation console is configured to display a measure value indicating the currently measured concentration, and wherein the instrumentation console is configured to receive a user input and set a threshold value, wherein the threshold value is a configured percentage of the currently measured concentration, and wherein the instrumentation console is configured to display the threshold value and the currently measured concentration simultaneously, and wherein the probe comprises a temperature sensor, and wherein the instrumentation console is configured to determine a current temperature of the probe and, where the current temperature falls outside of a usable range, disable use of the surgical apparatus, and where the temperature falls within a usable range, use the temperature to calibrate the currently measured concentration displayed during use of the probe to account for temperature related drift of the measured concentration.

EXAMPLE 11

An apparatus for detecting a locating medium in tissue, the apparatus comprising: a probe, wherein the probe includes a handle and a detector disposed on a distal end of the probe; and a console in communication with the probe, wherein the console includes a display having a first graphical representation and a second graphical representation, wherein the first graphical representation is configured to depict a count real-time count based on a signal from the detector, wherein the second graphical representation is configured to depict a target count.

EXAMPLE 12

The apparatus of Example 11, wherein the target count depicted by the second graphical representation corresponds to a user selectable target count.

EXAMPLE 13

The apparatus of Example 11, wherein the display further includes a third graphical representation, wherein the third graphical representation is configured to graphically depict a proportional relationship between the real-time count and the target count.

EXAMPLE 14

The apparatus of any one or more of Examples 11 through 13, wherein the target count is configured to be automatically set based on a predetermined percentage of a maximum count detected by the detector during a procedure.

EXAMPLE 15

The apparatus of Example 14, wherein the predetermined percentage is 10% of the maximum count.

EXAMPLE 16

The apparatus of Example 14, wherein the predetermined percentage is configured to be identified by an operator.

EXAMPLE 17

The apparatus of any one or more of Examples 11 through 16, wherein the console further includes a user input, wherein the user input is configured to set the target count upon receipt of a command input based on a predetermined percentage of the real-time count detected contemporaneously with the command input.

EXAMPLE 18

The apparatus of Example 17, wherein the predetermined percentage is 10% of the maximum count.

EXAMPLE 19

The apparatus of Example 17, wherein the predetermined percentage is configured to be identified by an operator.

EXAMPLE 20

The apparatus of Example 17, wherein the user input includes one or more of a push button, a foot pedal, and a voice detector.

EXAMPLE 21

The apparatus of any one or more of Examples 11 through 20, further comprising a temperature sensor and a processor, wherein the temperature sensor is configured to detect an operational temperature, wherein the processor is in communication with the temperature sensor and configured to adjust the signal of the detector to automatically compensate for temperature drift associated with the signal of the detector.

EXAMPLE 22

An apparatus for locating lymph nodes, the apparatus comprising: a probe having a handle and a proximity sensor disposed on a distal end of the handle, wherein the proximity sensor is configured to sense the strength of a signal received from a source disposed within tissue; and a user interface in communication with the probe, wherein the user interface includes a first indicator and a second indicator, wherein the first indicator is configured to display the signal sensed by the proximity sensor continuously and in real-time, wherein the second indicator is configured to display a target value relative to the signal sensed by the proximity sensor.

EXAMPLE 23

The apparatus of Example 22, wherein the user interface further comprises a third indicator, wherein the third indicator is configured to provide a visual indication of a difference between the signal sensed by the proximity sensor and the target value.

EXAMPLE 24

The apparatus of Examples 22 or 23, wherein at least a portion of the user interface is incorporated into the handle of the probe.

EXAMPLE 25

The apparatus of any one or more of Examples 22 through 24, wherein the user interface further includes a threshold button, wherein the threshold button is configured to initiate a set threshold sequence where the target value is set to the signal sensed by the proximity sensor upon initiation of the set threshold sequence reduced by a predetermined amount set by an operator.

EXAMPLE 26

The apparatus of any one or more of Examples 22 through 24, wherein the user interface further includes a threshold button, wherein the threshold button is configured to initiate a set threshold sequence where the target value is set to 10% of the signal sensed by the proximity sensor upon initiation of the set threshold sequence.

EXAMPLE 27

The apparatus any one or more of Examples 22 through 26, wherein the sensor is detachably coupled to the handle.

EXAMPLE 28

A system, comprising: a hand-held probe including: a detector configured to generate a signal proportionate to the proximity of concentration of a tracing medium positioned proximate a portion of the detector, a handle, wherein the detector extends from a distal end of the handle, and a probe link configured to transmit data associated with the signal generated by the detector; and a controller including: a housing, a controller link disposed within the housing and configured to receive data from the probe link, a receiver in communication with the controller link, and a display in communication with the receiver, wherein the receiver is configured to drive the display to generate a first indicator and a second indicator on the display based on data received from the probe link, wherein the first indicator corresponds to a current signal generated by the detector, wherein the second indicator corresponds to a target signal.

EXAMPLE 29

The system of Example 28, wherein the receiver is configured to generate the target signal automatically based on calculating 10% of a maximum signal value generated by the detector during a predetermined period of time.

EXAMPLE 30

The system of Example 29, wherein the predetermined period of time corresponds to either the duration of a procedure or the duration during which an operator input is received by the receiver.

EXAMPLE 31

The system of any one or more of Examples 28 through 30, further comprising a temperature sensor and a processor, wherein the temperature sensor is configured to detect an operational temperature, wherein the processor is in communication with the temperature sensor and configured to adjust data from the probe link to automatically compensate for temperature drift of the signal generated by the detector.

The invention claimed is:

1. A system, comprising:
   (a) an instrumentation console including a display;
   (b) a probe in communication with the instrumentation console, the probe including a magnetic sensor configured to detect a magnetic field, the display being configured to depict a signal generated by the magnetic sensor based on proximity of the magnetic sensor to one or more magnetic particles; and
   (c) a temperature sensor, the temperature sensor being disposed within a portion of the probe, the temperature sensor being in communication with the instrumentation console, the instrumentation console being configured to adjust one or more operational parameters of the system based on a temperature detected by the temperature sensor.

2. The system of claim 1, the probe including a probe tip, the probe tip housing at least a portion of the magnetic sensor, the temperature sensor being proximate the probe tip.

3. The system of claim 1, the probe including a probe tip, the probe tip housing at least a portion of the magnetic sensor such that the probe tip is configured to detect and measure the strength of the magnetic field in an area surrounding the probe tip, the temperature sensor being configured to detect the temperature within the area surrounding the probe tip.

4. The system of claim 1, the probe including a probe tip, the probe tip housing at least a portion of the magnetic sensor, the probe tip further housing at least a portion of the temperature sensor.

5. The system of claim 1, the instrumentation console being configured to disable use of the probe when the temperature detected by the temperature sensor is below or exceeds a predetermined temperature threshold.

6. The system of claim 1, the instrumentation console being configured to disable use of the probe when the temperature detected by the temperature sensor is within one or more predetermined temperature ranges.

7. The system of claim 6, the one or more predetermined temperature ranges including a first temperature range and a second temperature range, the first temperature range being a low temperature range corresponding to the temperature being below an operational threshold, the second temperature range being a high temperature range corresponding to the temperature being above an operational threshold.

8. The system of claim 6, the instrumentation console being configured to automatically compensate for temperature drift of the signal generated by the magnetic sensor based on the temperature detected by the temperature sensor when the temperature detected by the temperature sensor is within a predetermined operational temperature range.

9. The system of claim 1, the instrumentation console being configured to automatically compensate for temperature drift of the signal generated by the magnetic sensor based on the temperature detected by the temperature sensor.

10. An apparatus for detecting and measuring proximity to an injected magnetic material, the apparatus comprising:
   (a) a probe, the probe including an elongate body and a distal probe tip, the distal probe tip including a magnetic sensor configured to emit a signal proportional to the proximity of the distal probe tip to the injected magnetic material; and
   (b) a temperature sensor proximate the distal probe tip, the temperature sensor being configured to detect a temperature proximate the probe tip corresponding to a probe temperature.

11. The apparatus of claim 10, further comprising one or more processors, the one or more processors being in communication with the magnetic sensor and the temperature sensor, the one or more processors being configured to adjust the signal emitted by the magnetic sensor based on the temperature detected by the temperature sensor.

12. The apparatus of claim 10, at least a portion of the temperature sensor being integrated into the distal probe tip.

13. The apparatus of claim 10, further comprising a display, the display being configured to depict a real-time signal strength corresponding to the signal emitted by the magnetic sensor and adjusted based on the temperature detected by the temperature sensor.

14. The apparatus of claim 10, further comprising one or more processors and a display, the one or more processors being in communication with the magnetic sensor and the temperature sensor, the one or more processors being configured to adjust the signal emitted by the magnetic sensor based on the temperature detected by the temperature sensor to generate a real-time adjusted signal strength, the display being configured to depict a graphical representation corresponding to the real-time adjusted signal strength.

15. A system, comprising:
   (a) a probe, the probe including:
      (i) an elongate body,
      (ii) a distal probe tip,
      (iii) a magnetic sensor proximate the distal probe tip, the magnetic sensor being configured to generate a signal corresponding to the proximity of the magnetic sensor relative to one or more magnetic particles, and
      (iv) a temperature sensor disposed in the elongate body or the distal probe tip, the temperature sensor being configured to detect an operational temperature; and
   (b) a console including a display, the console being in communication with the probe, the display having a first graphical representation and a second graphical representation, the first graphical representation being configured to depict a real-time signal strength corresponding to the signal generated by the magnetic sensor, the second graphical representation being configured to depict a target signal strength, the console being configured to adjust the real-time signal strength depicted by the first graphical representation based on the operational temperature detected by the temperature sensor.

16. The system of claim 15, the console being configured to reduce the real-time signal strength depicted by the first graphical representation based on the operational temperature detected by the temperature sensor.

17. The system of claim 15, the console being configured to continuously adjust the real-time signal strength depicted by the first graphical representation based on the operational temperature detected by the temperature sensor.

18. The system of claim 15, the temperature sensor being proximate the magnetic sensor.

19. The system of claim 15, the temperature sensor being integrated into a portion of the magnetic sensor.

20. The system of claim 15, the console being configured to disable the probe upon detection of the operational temperature being above a predetermined threshold, the console being further configured to disable the probe upon detection of the operational temperature being below a predetermined threshold.

* * * * *